(12) United States Patent
Shafrir et al.

(10) Patent No.: US 10,842,639 B2
(45) Date of Patent: Nov. 24, 2020

(54) IMPLANT

(71) Applicant: SPINOL, LTD., Modi'in-Macabim-Re'ut (IL)

(72) Inventors: Roey Shafrir, Modi'in-Macabim-Re'ut (IL); Haim Shnider, Netanya (IL); Shahar Dror, Tel Aviv (IL)

(73) Assignee: Spinol, Ltd., Modi'in-Macabim-Re'ut (IL)

( * ) Notice: Subject to any disclaimer, the term of this patent is extended or adjusted under 35 U.S.C. 154(b) by 0 days.

(21) Appl. No.: 16/480,705

(22) PCT Filed: Mar. 10, 2019

(86) PCT No.: PCT/IL2019/050263
§ 371 (c)(1),
(2) Date: Jul. 25, 2019

(87) PCT Pub. No.: WO2019/175862
PCT Pub. Date: Sep. 19, 2019

(65) Prior Publication Data
US 2020/0268521 A1    Aug. 27, 2020

Related U.S. Application Data

(60) Provisional application No. 62/643,236, filed on Mar. 15, 2018.

(51) Int. Cl.
*A61F 2/44* (2006.01)
*A61F 2/30* (2006.01)

(52) U.S. Cl.
CPC .............. *A61F 2/44* (2013.01); *A61F 2/3094* (2013.01); *A61F 2002/30092* (2013.01);
(Continued)

(58) Field of Classification Search
CPC ..... A61F 2002/4435; A61F 2/44; A61F 2/442
See application file for complete search history.

(56) References Cited

U.S. PATENT DOCUMENTS 9,526,623 B2    12/2016   Drori et al.
2003/0074075 A1*  4/2003   Thomas, Jr. ............ A61F 2/442
                                                  623/17.16
(Continued)

FOREIGN PATENT DOCUMENTS

WO    2009/033100 A1    3/2009
WO    2010/141910 A1    12/2010

OTHER PUBLICATIONS

International search report for parent PCT application PCT/IL2019/050263, dated Jul. 11, 2019 by European Patent Office.
(Continued)

*Primary Examiner* — Julianna N Harvey
(74) *Attorney, Agent, or Firm* — Chanoch Kahn; Simon Kahn

(57) ABSTRACT

An implant constituted of: a body exhibiting a longitudinal axis; proximal arms extending from the body, each of the proximal arms extending in a respective direction and exhibiting a respective acute angle with the longitudinal axis, the body positioned between the proximal arms; distal arms extending from the body, each of the distal arms extending in a respective direction and exhibiting a respective acute angle with the longitudinal axis, the respective directions of extension of the distal arms generally opposing the respective directions of extension of the proximal arms, the body positioned between the distal arms; and intermediate arm assemblies extending from the body, each of the intermediate arm assemblies extending in a respective direction rotated about the longitudinal axis from the respective extension directions of the proximal arms and exhibiting a
(Continued)

respective acute angle with the longitudinal axis, the body positioned between the intermediate arm assemblies.

9 Claims, 11 Drawing Sheets

(52) U.S. Cl.
CPC ............ *A61F 2002/30131* (2013.01); *A61F 2002/30171* (2013.01); *A61F 2002/30306* (2013.01); *A61F 2002/4435* (2013.01)

(56) References Cited

U.S. PATENT DOCUMENTS

| | | | | |
|---|---|---|---|---|
| 2008/0071356 A1* | 3/2008 | Greenhalgh | .......... | A61F 2/4611 623/1.16 |
| 2010/0131014 A1* | 5/2010 | Peyrot | ................ | A61B 17/7266 606/300 |
| 2013/0338778 A1* | 12/2013 | Drori | ....................... | A61F 2/442 623/17.16 |
| 2015/0094815 A1* | 4/2015 | Drori | .................... | A61F 2/4611 623/17.16 |
| 2015/0141994 A1* | 5/2015 | Cheney | .............. | A61B 17/7266 606/63 |

OTHER PUBLICATIONS

Written opinion of international search report for parent PCT application PCT/IL2019/050263, dated Jul. 11, 2019 by European Patent Office.

* cited by examiner

IMPLANT

FIELD OF THE INVENTION

The invention relates generally to the field of implantable devices for the closure of biological defects, and more particularly to an implant arranged to securely seal an intervertebral disc defect.

CROSS-REFERENCE TO RELATED APPLICATIONS

The present application claims priority from U.S. provisional patent application Ser. 62/643,236, filed Mar. 15, 2018, and entitled "IMPLANT", the entire contents of which incorporated herein by reference.

BACKGROUND OF THE INVENTION

The human spine, known technically as the vertebral column, is constituted of a plurality of articulating vertebrae, and extending downwards towards fused vertebrae in the sacrum and coccyx. Using standard anatomical terminology, the vertebral column is found in the dorsal aspect of the torso. The articulating vertebrae are separated from adjacent vertebrae on either side by an intervertebral disc which forms a cartilaginous joint to allow slight movement of the vertebrae, and further acts to hold the various vertebrae together so as to form the vertebral column.

Each intervertebral disc comprises an outer annulus fibrosus, often simply called the annulus, which surrounds and contains the nucleus pulposus which is a jelly-like substance which functions to distribute hydraulic pressure within each intervertebral disc under compressive loads. In the event of an intervertebral disc defect, such as a prolapsed or herniated disc, the nucleus pulposus is forced out through the defect of the annulus, and may apply pressure to nearby nerves or to the spinal cord. In severe cases the escaping nucleus pulposus may cause chemical irritation of nearby nerve roots. Protrusion of the nucleus pulposus may be variously referred to as a disc bulge, a herniated disc, a ruptured disc or a sequestered disc, depending on the specific diagnosis.

In order to avoid confusion in describing medical devices, certain fixed terminology is utilized. In particular, the term proximal usually means closer to the surgeon, unless otherwise stated, and the word distal usually means further removed from the surgeon, unless otherwise stated. Surgery to repair a defect in the annulus is usually performed from the patient's dorsal side, i.e. from the back, and thus the terms proximal and distal are understood with the surgeon approaching from the patient's back; however this is not meant to be limiting in any way. In the event of surgery performed ventrally, the terms need to be understood in relation to a dorsal operation.

While various schemes for repair of the annulus defects are known, one common solution is a surgical procedure known as discectomy which involves the surgical removal of the herniated disc material. Discectomy is often performed in conjunction with a laminectomy, where a small piece of bone, known as the lamina, is removed from the affected vertebra, allowing the surgeon to better see and access the area of disc herniation.

One problem with the above procedure is that additional nucleus pulposus material may be ejected from the annulus over time by the unsealed defect in the annulus, which is not sealed by the discectomy. Thus, a device and associated procedure is required to seal the annulus defect. Various devices and procedures are known to the prior art, including without limitation, U.S. patent application publication S/N US 2011/0282456, published Nov. 17, 2011 to Shafrir et al., and entitled "Implantable Device for Sealing a Spinal Annular Fissure Tear and Method for Deploying the Same", the entire contents of which are incorporated herein by reference. One issue not fully addressed by the above subject patent publication, and other devices of the prior art, is the issue of ejection, i.e. the tendency of any device placed in the annulus to be ejected over time responsive to forces developed in the remaining nucleus pulposus material.

Certain improved devices are described in: U.S. patent application publication S/N US 2013/0338778, published Dec. 19, 2013 and entitled "Spinal Disc Annulus Closure Device", the entire contents of which are incorporated herein by reference; and U.S. Pat. No. 9,526,623, granted Dec. 27, 2016 and entitled "Spinal Disc Annulus Closure Device", the entire contents of which are incorporated herein by reference. One of the challenges of such a device is to stand up to strong hydrostatic ejection forces while not interfering with a full range of motion of the vertebral column over an expected patient lifetime. Unfortunately, such devices have shown difficulties with maintaining structural integrity over an expected patient lifetime.

What is desired, and not supplied by the prior art, is a device arranged to: seal the annulus against further release of nucleus pulposus material through the defect; resist ejection from the annulus; allow for a full range of motion of the vertebral column over an expected patient lifetime without fatigue failure; and be easily manipulated to an insertion size.

SUMMARY

Accordingly, it is a principal object of the present invention to overcome at least some of the disadvantages of the prior art. In certain embodiments this is provided by an implant, the implant comprising: a body exhibiting a longitudinal axis; a pair of proximal arms extending from the body, each of the pair of proximal arms extending in a respective direction and exhibiting a respective acute angle with the longitudinal axis, the body positioned between the pair of proximal arms; a pair of distal arms extending from the body, each of the pair of distal arms extending in a respective direction and exhibiting a respective acute angle with the longitudinal axis, the respective directions of extension of the pair of distal arms generally opposing the respective directions of extension of the pair of proximal arms, the body positioned between the pair of distal arms; and a pair of intermediate arm assemblies extending from the body, each of the pair of intermediate arm assemblies extending in a respective direction rotated about the longitudinal axis from the respective extension directions of the pair of proximal arms and exhibiting a respective acute angle with the longitudinal axis, the body positioned between the pair of intermediate arm assemblies.

In one embodiment, each of the pair of intermediate arm assemblies comprises a pair of intermediate arms each exhibiting a first end and a second end opposing the first end, each of the intermediate arms respectively extending from the body at the first end, and wherein the second ends of respective constituent intermediate arms of each pair of intermediate arm assemblies are separated by a predetermined distance. In one further embodiment, respective constituent intermediate arms of each of the pair of intermediate arm assemblies curve away from each other.

In another embodiment, each of the pair of intermediate arm assemblies exhibits: a generally convexingly curved face facing the extension directions of the pair of proximal arms; and a generally concavingly curved face facing the extension directions of the pair of distal arms. In one further embodiment, each of the pair of intermediate arm assemblies comprises a plurality of stacked layers, each of the plurality of stacked layers exhibiting a generally concavingly curved face and a generally convexingly curved face opposing the generally concavingly curved face, wherein each of the plurality of stacked layers is adjacent to another of the plurality of stacked layers such that the generally concavingly curved face of a first of the adjacent layers faces the generally convexingly curved face of a second of the adjacent layers, and wherein the first of the adjacent layers arranged to push against the second of the adjacent layers responsive to a force being applied to the convexingly curved face of the first of the adjacent layers.

In one yet further embodiment, each of the plurality of stacked layers comprises a first section, a second section and a stress release notch between the first section and the second section. In another yet further embodiment, each of the pair of proximal arms and each of the pair of distal arms extend linearly from a respective first end to a respective second end, the respective first ends opposing the respective second ends.

In one embodiment, a first of one of the pair of proximal arms and pair of distal arms exhibits an opening, wherein a first of the other of the pair of proximal arms and the pair of distal arms is arranged to extend through the opening. In another embodiment, each of the pair of proximal arms exhibits a first end and a second end opposing the first end, each of the pair of proximal arms respectively extending from the body at the first end, wherein the second end of one of the pair of proximal arms exhibits a first section, a second section and a third section, the second section being between the first section and the third section, and wherein a width of the second section is less than a width of each of the first section and the third section, the widths of the first, second and third sections defined orthogonally to a longitudinal axis of the one of the pair of proximal arms.

In one embodiment, each of the pair of proximal arms exhibits a first end and a second end opposing the first end, each of the pair of proximal arms respectively extending from the body at the first end, wherein each of the pair of distal arms exhibits a first end and a second end opposing the first end, each of the pair of distal arms respectively extending from the body at the first end, wherein the body exhibits a first end and a second end opposing the first end, each of the pair of proximal arms extending from the second end of the body towards a respective plane, the respective plane orthogonal to the longitudinal axis of the body and meets the first end of the body, and wherein each of the pair of distal arms extends from the first end of the body towards a respective plane, the respective plane orthogonal to the longitudinal axis of the body and meets the second end of the body. In one further embodiment, the implant further comprises a connection member, the connection member exhibiting a first end and a second end opposing the first end, wherein the body exhibits a first face extending from the first end of the body to the second end of the body, and a second face opposing the first face, the second face extending from the first end of the body to the second end of the body, wherein one of the first end and the second end of the body exhibits an opening extending from the first face to the second face, and wherein the first end of one of: the constituent arms of the pair of proximal arms; and the constituent arms of the pair of distal arms, exhibits a respective opening, the connection member further arranged to extend through the respective openings and through the opening of the body.

In another further embodiment, the body exhibits a first face and a second face opposing the first face, each of the first face and the second face exhibiting a respective acute angle with the longitudinal axis of the body at one of the first end and second end thereof, each of the respective angles of the first face and the second face being equal to the angle between the longitudinal axis of the body and the respective one of the proximal arms and distal arms extending therefrom.

In one embodiment, each of the pair of intermediate arm assemblies comprises a pair of intermediate arms each exhibiting a first end and a second end opposing the first end, each of the intermediate arms respectively extending from the body at the first end of the body, wherein the second ends of respective constituent intermediate members of each pair of intermediate arm assemblies are separated by a predetermined distance, wherein the body comprises a first section and a second section, each of the first section and the second section exhibiting a first face and a second face opposing the first planar face, the first face of the first section arranged to meet the first face of the second section, wherein a first of each of the constituent pair of intermediate arms and the first section are formed of a respective portion of material such that the first of each of the pair of constituent intermediate arms is continuous with the first section, a first of each of the pair of proximal arms and the pair of distal arms attached to the first section. In one further embodiment, a second of each of the constituent pair of intermediate arms and the second section are formed out of a respective portion of material such that the second of each of the pair of constituent intermediate arms is continuous with the second section, a second of each of the pair of proximal arms and the pair of distal arms attached to the second section.

In one independent embodiment a method for production of an implant is provided, the method comprising: providing a bio-compatible material; forming from the provided bio-compatible material a body exhibiting a longitudinal axis; forming from the provided bio-compatible material a pair of proximal arms extending from the body, each of the pair of proximal arms extending in a respective direction and exhibiting a respective acute angle with the longitudinal axis, the body positioned between the pair of proximal arms; forming from the provided bio-compatible material a pair of distal arms extending from the body, each of the pair of distal arms extending in a respective direction and exhibiting a respective acute angle with the longitudinal axis, the respective directions of extension of the pair of distal arms generally opposing the respective directions of extension of the pair of proximal arms, the body positioned between the pair of distal arms; and forming from the provided bio-compatible material a pair of intermediate arm assemblies extending from the body, each of the pair of intermediate arm assemblies extending in a respective direction rotated about the longitudinal axis from the respective extension directions of the pair of proximal arms and exhibiting a respective acute angle with the longitudinal axis, the body positioned between the pair of intermediate arm assemblies.

In one embodiment, each of the pair of intermediate arm assemblies comprises a pair of intermediate arms each exhibiting a first end and a second end opposing the first end, each of the intermediate arms respectively extending from the body at the first end, and wherein the second ends of respective constituent intermediate members of each pair of intermediate arm assemblies are separated by a predetermined distance. In one further embodiment, respective constituent intermediate arms of each of the pair of intermediate arm assemblies curve away from each other.

In another embodiment, each of the pair of intermediate arm assemblies exhibits: a generally convexingly curved face facing the extension directions of the pair of proximal arms; and a generally concavingly curved face facing the extension directions of the pair of distal arms. In one further embodiment, wherein each of the pair of intermediate arm assemblies comprises a plurality of stacked layers, each of the plurality of stacked layers exhibiting a generally concavingly curved face and a generally convexingly curved face opposing the generally concavingly curved face, wherein each of the plurality of stacked layers is adjacent to another of the plurality of stacked layers such that the generally concavingly curved face of a first of the adjacent layers faces the generally convexingly curved face of a second of the adjacent layers, and wherein the first of the adjacent layers arranged to push against the second of the adjacent layers responsive to a force being applied to the convexingly curved face of the first of the adjacent layers.

In another further embodiment, each of the plurality of stacked layers comprises a first section, a second section and a stress release notch between the first section and the second section. In one yet further embodiment, each of the pair of proximal arms and each of the pair of distal arms extend linearly from a respective first end to a respective second end, the respective first ends opposing the respective second ends.

In one embodiment, a first of one of the pair of proximal arms and pair of distal arms exhibits an opening, and wherein a first of the other of the pair of proximal arms and the pair of distal arms is arranged to extend through the opening. In another embodiment, each of the pair of proximal arms exhibits a first end and a second end opposing the first end, each of the pair of proximal arms respectively extending from the body at the first end, wherein the second end of one of the pair of proximal arms exhibits a first section, a second section and a third section, the second section being between the first section and the third section, and wherein a width of the second section is less than a width of each of the first section and the third section, the widths of the first, second and third sections defined orthogonally to a longitudinal axis of the one of the pair of proximal arms.

In one embodiment, each of the pair of proximal arms exhibits a first end and a second end opposing the first end, each of the pair of proximal arms respectively extending from the body at the first end, wherein each of the pair of distal arms exhibits a first end and a second end opposing the first end, each of the pair of distal arms respectively extending from the body at the first end, wherein the body exhibits a first end and a second end opposing the first end, each of the pair of proximal arms extending from the first end of the body towards a respective plane, the respective plane orthogonal to the longitudinal axis of the body and meets the second end of the body, and wherein each of the pair of distal arms extends from the second end of the body towards a respective plane, the respective plane orthogonal to the longitudinal axis of the body and meets the first end of the body. In one further embodiment, the method further comprises forming from the bio-compatible material a connection member, the connection member exhibiting a first end and a second end opposing the first end, wherein the body exhibits a first face extending from the first end of the body to the second end of the body, and a second face opposing the first face, the second face extending from the first end of the body to the second end of the body, wherein one of the first end and the second end of the body exhibits an opening extending from the first face to the second face, and wherein the first end of one of: the constituent arms of the pair of proximal arms; and the constituent arms of the pair of distal arms, exhibits a respective opening, the connection member further arranged to extend through the respective openings and through the opening of the body.

In another further embodiment, the body exhibits a first face and a second face opposing the first face, each of the first face and the second face exhibiting a respective angle with the longitudinal axis of the body at one of the first end and second end thereof, each of the respective angles of the first face and the second face being equal to the angle between the longitudinal axis of the body and the respective one of the proximal arms and distal arms extending therefrom.

In one embodiment, each of the pair of intermediate arm assemblies comprises a pair of intermediate arms each exhibiting a first end and a second end opposing the first end, each of the intermediate arms respectively extending from the body at the first end of the body, wherein the second ends of respective constituent intermediate members of each pair of intermediate arm assemblies are separated by a predetermined distance, wherein the body comprises a first section and a second section, each of the first section and the second section exhibiting a first planar face and a second planar face opposing the first planar face, the first planar face of the first section arranged to meet the first planar face of the second section, wherein a first of each of the constituent pair of intermediate arms and the first section are formed of a respective portion of material such that the first of each of the pair of constituent intermediate arms is continuous with the first section, a first of each of the pair of proximal arms and the pair of distal arms attached to the first section. In one further embodiment, a second of each of the constituent pair of intermediate arms and the second section are formed out of a respective portion of material such that the second of each of the pair of constituent intermediate arms is continuous with the second section, a second of each of the pair of proximal arms and the pair of distal arms attached to the second section.

Additional features and advantages of the invention will become apparent from the following drawings and description.

BRIEF DESCRIPTION OF THE DRAWINGS

For a better understanding of various embodiments of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

Figure 1A:
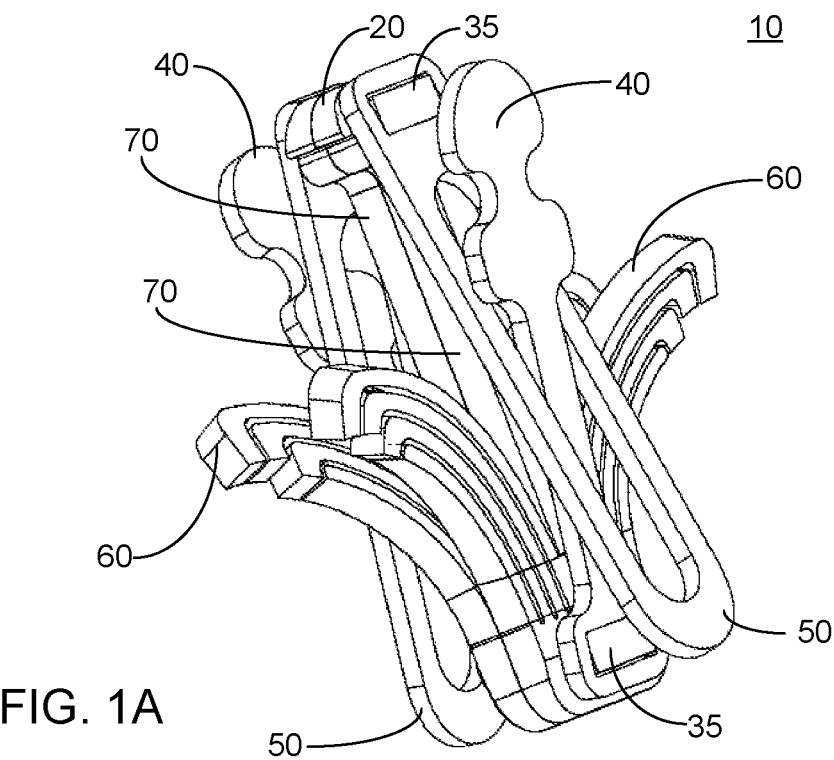
FIGS. 1A-1N illustrate various high level views of an implant for closure of a biological defect, in a deployed configuration, in accordance with certain embodiments.

Before explaining at least one embodiment in detail, it is to be understood that the invention is not limited in its application to the details of construction and the arrangement of the components set forth in the following description or illustrated in the drawings. The invention is applicable to other embodiments being practiced or carried out in various ways. Also, it is to be understood that the phraseology and terminology employed herein is for the purpose of description and should not be regarded as limiting.

Figure 1B:
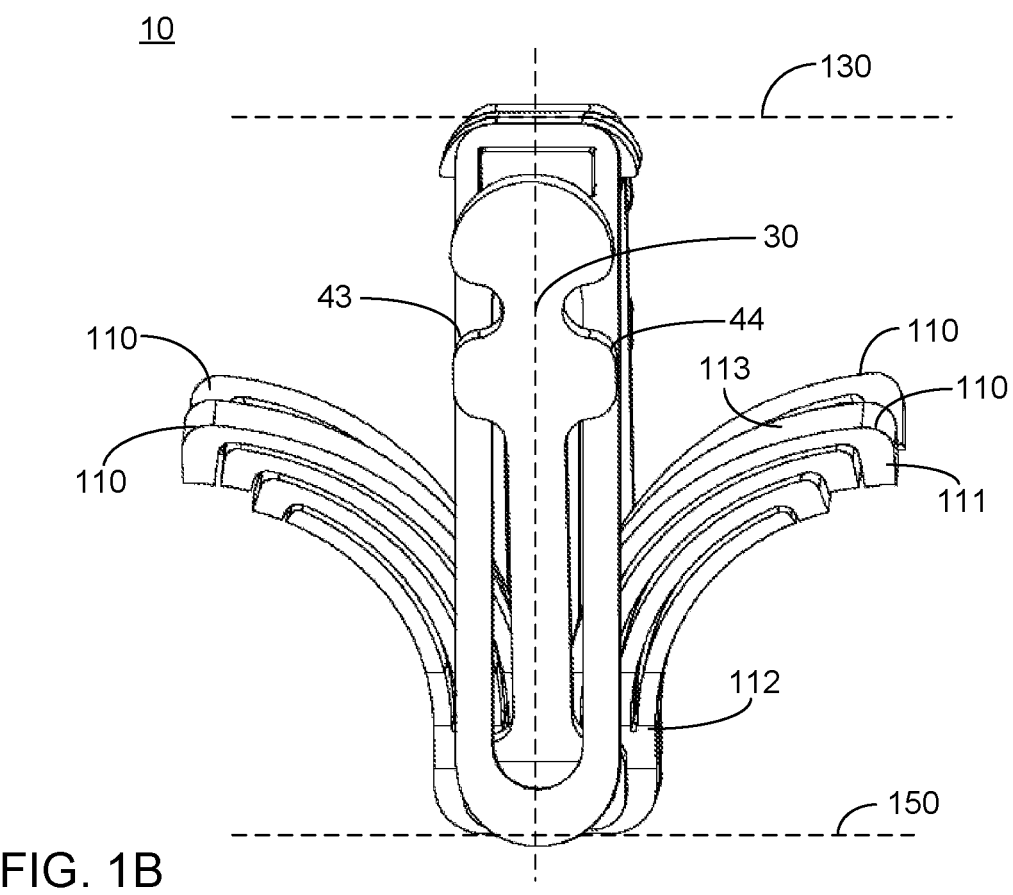
Figure 1C:
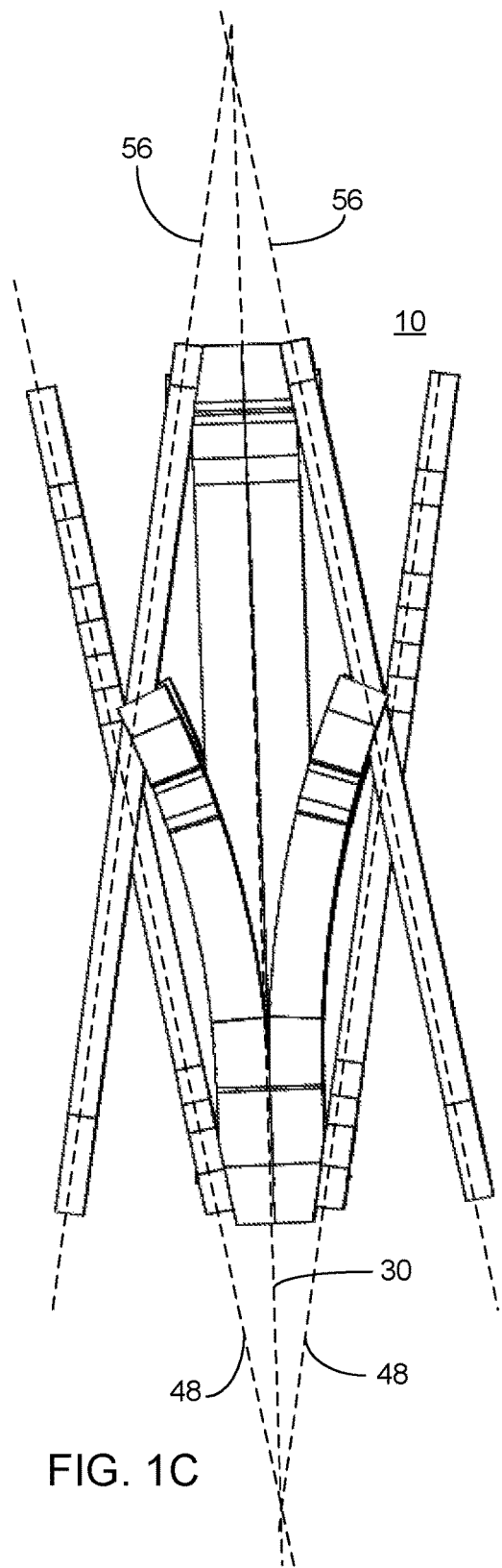
Figure 1D:
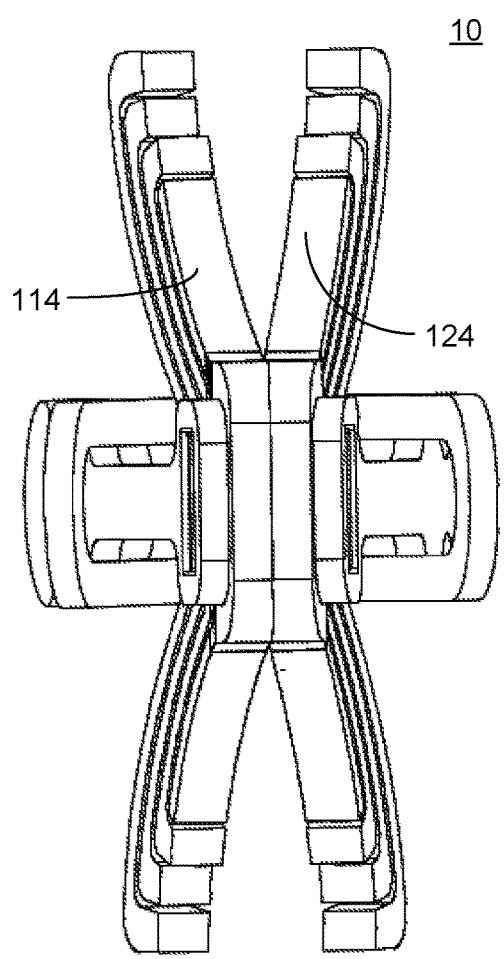
Figure 1E:
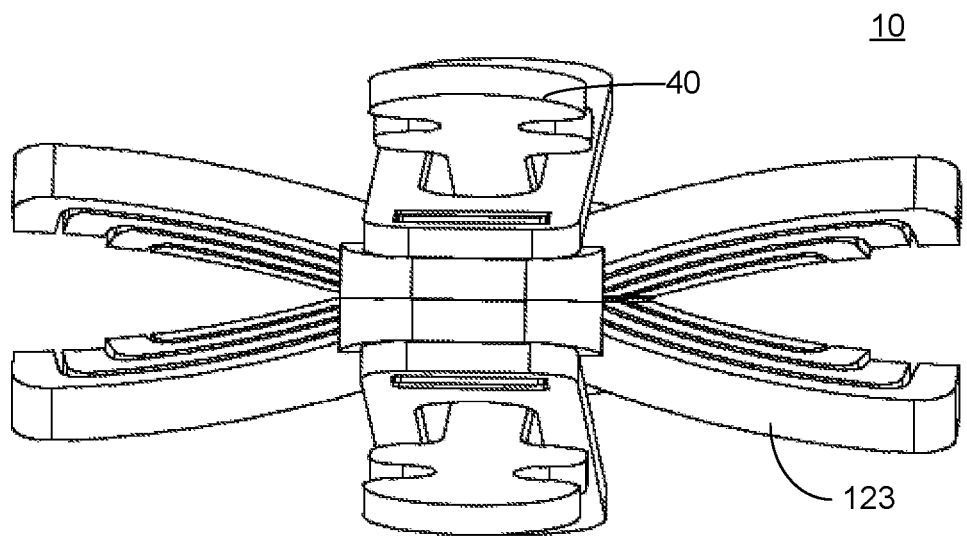
Figure 1F:
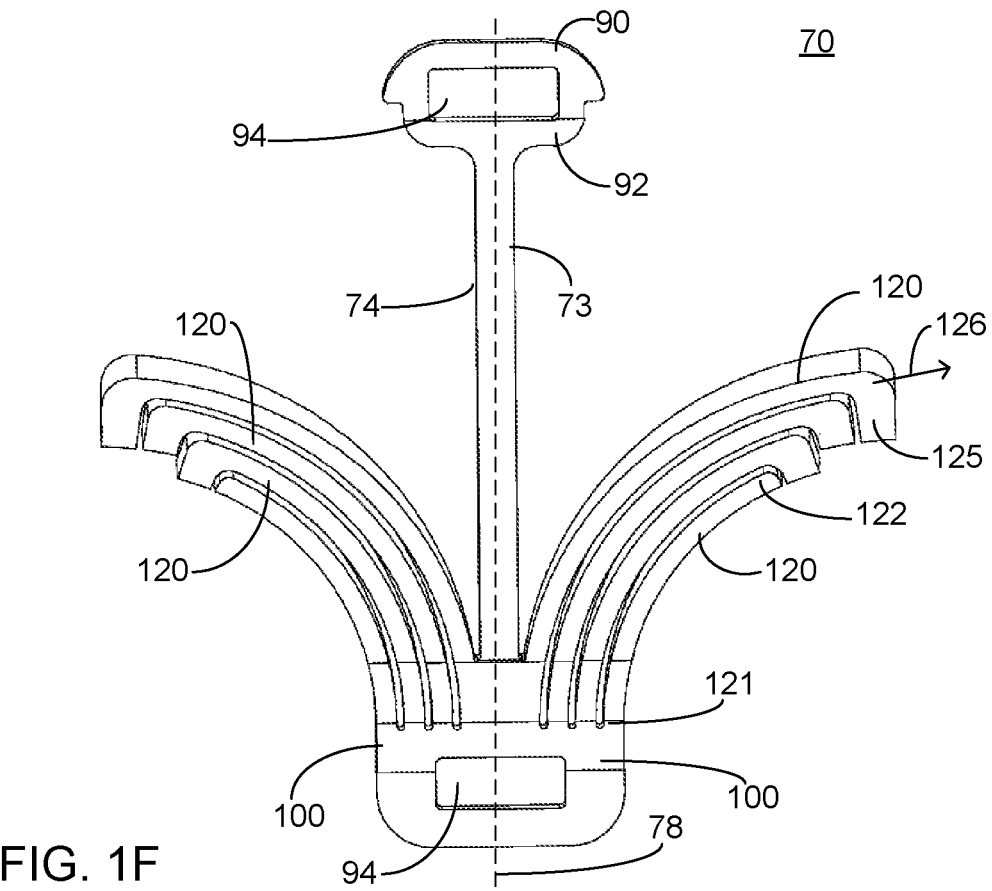
Figure 1G:
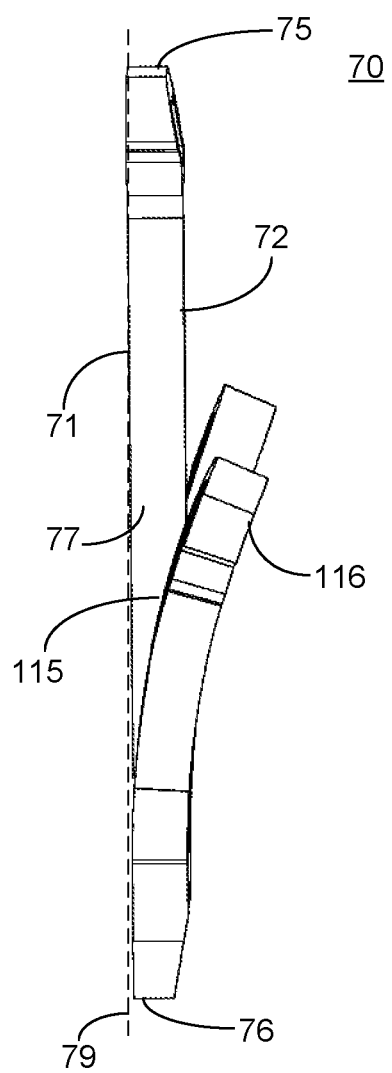
Figure 1H:
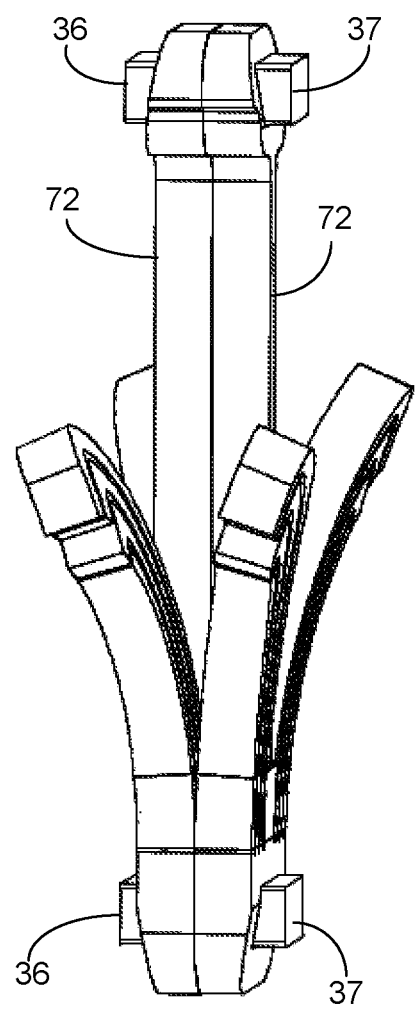
Figure 1I:
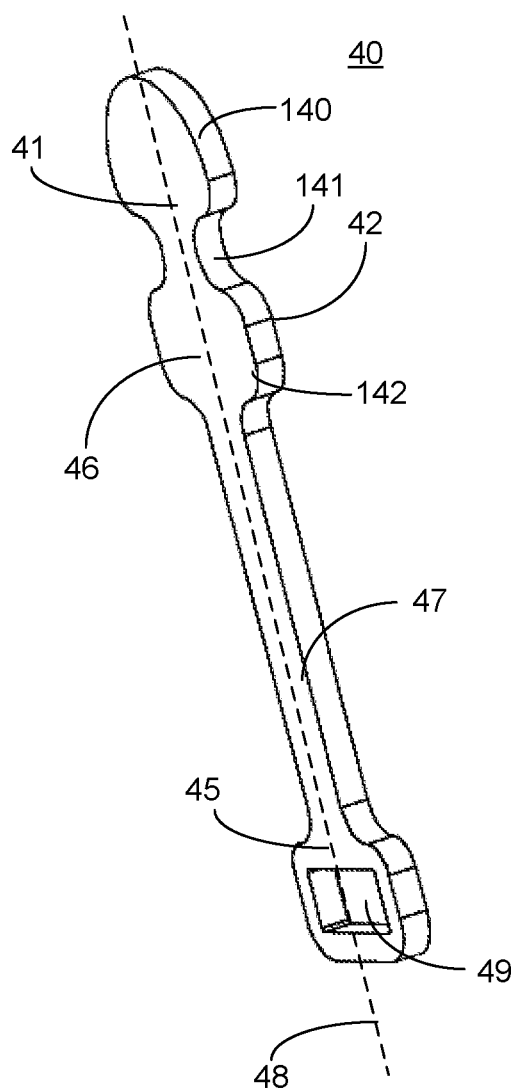
Figure 1J:
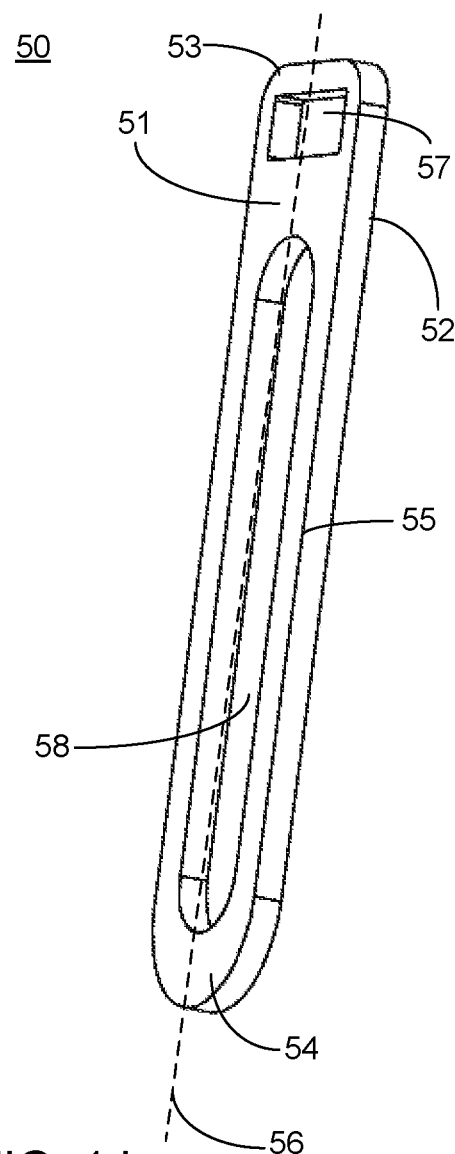
Figure 1K:
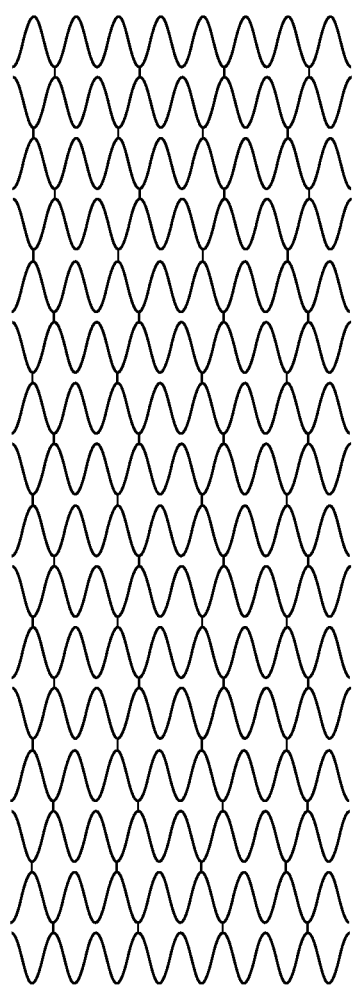
Figure 1L:
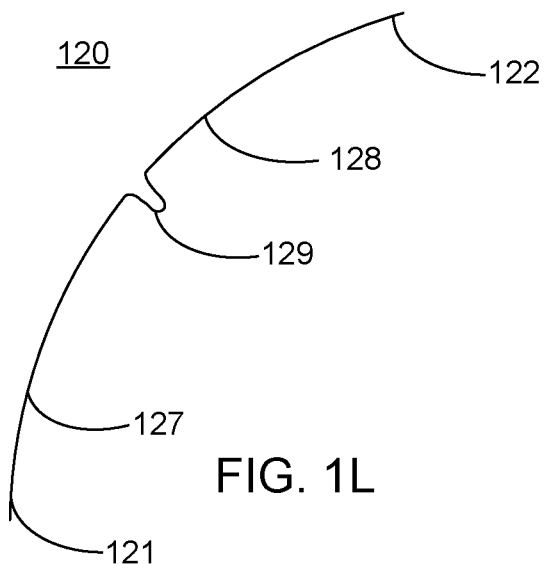
Figure 1M:
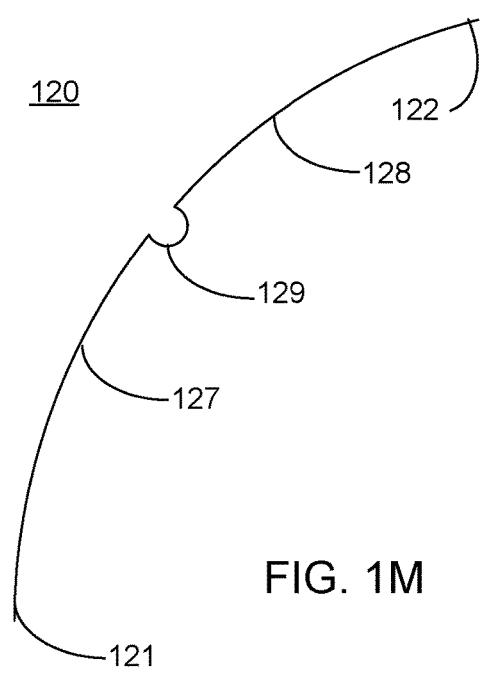
Figure 1N:
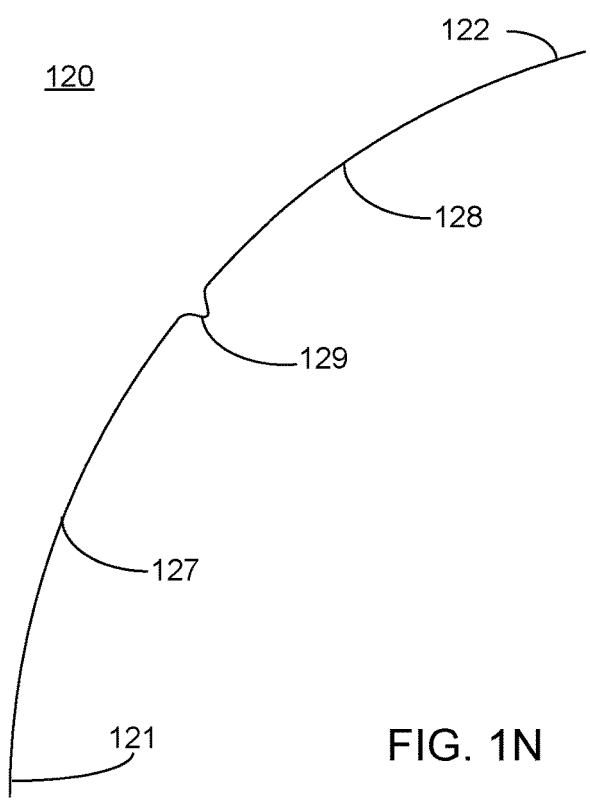

FIGS. 1A-1N illustrate various high level views of an implant 10. Implant 10 comprises: a body 20 exhibiting a longitudinal axis 30; a pair of connection members 35, each exhibiting a first end 36 and a second end 37; a pair of proximal arms 40; a pair of distal arms 50; and a pair of intermediate arm assemblies 60. Body 20 comprises a pair of sections 70. Each proximal arm 40 exhibits: a first face 41; a second face 42 opposing first face 41; a first side 43 generally orthogonal to first face 41 and second face 42; a second side 44 opposing first side 43; a first end 45; a second end 46 opposing first end 45; a middle portion 47 between first end 45 and second end 46; and a longitudinal axis 48. Each distal arm 50 exhibits: a first face 51; a second face 52 opposing first face 51; a first end 53; a second end 54 opposing first end 53; a middle portion 55 between first end 53 and second end 54; and a longitudinal axis 56. Each section 70 exhibits: a first face 71; a second face 72 opposing first face 71; a first side 73 generally orthogonal to first face 71 and second face 72; a second side 74 opposing first side 73; a first end 75; a second end 76 opposing first end 75; a middle portion 77 between first end 75 and second end 76; and a longitudinal axis 78. Implant 10 is formed from a bio-compatible material. In one non-limiting embodiment, sections 70 and intermediate arm assemblies 60 are formed of a shape memory alloy, optionally Nitinol.

FIG. 1A illustrates a high level perspective view of implant 10, FIG. 1B illustrates a high level general front view of implant 10, FIG. 1C illustrates a high level side view of implant 10, FIG. 1D illustrates a high level bottom view of implant 10, FIG. 1E illustrates a high level top view of implant 10, FIG. 1F illustrates a high level front view of a section 70, FIG. 1G illustrates a high level side view of a section 70, FIG. 1H illustrates a high level perspective view of a pair of sections 70 attached to each other, FIG. 1I illustrates a high level perspective view of a proximal arm 40, FIG. 1J illustrates a high level perspective view of a distal arm 50, FIG. 1K illustrates a high level schematic view of a mesh configuration of a portion of an intermediate arm assembly 60 and FIGS. 1L-1N illustrate high level side views of various alternate embodiments of parts of intermediate arm assemblies 60. FIGS. 1A-1N are described together.

In one embodiment, first end 75 of each section 70 exhibits: a first section 90; a second section 92; and an opening 94 extending from first face 71 to second face 72. Second section 92 of first end 75 is between first section 90 and middle portion 77. Second section 92 extends orthogonally to longitudinal axis 78 past first side 73 and past second side 74 of middle portion 77. Similarly, first section 90 extends orthogonally to longitudinal axis 78 past first side 73 and past second side 74 of second section 92. In one embodiment, first section 90 extends past each of first side 73 and second side 74 of second section 92 by 0.1-3 millimeters. First section 90 and second section 92 surround opening 94. Second face 72 of first end 75 exhibits a predetermined acute angle with longitudinal axis 78 such that first side 73 and second side 74 of first end 75 are each generally shaped as a right-angled trapezoid. In one non-limiting embodiment, the predetermined acute angle between second face 72 of first end 75 and longitudinal axis 78 is between 5-30 degrees.

Second end 76 of each section 70 extends orthogonally to longitudinal axis 78 past first side 73 into a respective extension portion 100 and extends orthogonally to longitudinal axis 78 past second side 74 of middle portion 77 into a respective extension portion 100. An opening 94 extends through second end 76 from first face 71 to second face 72. Second face 72 of second end 76 exhibits a predetermined acute angle with longitudinal axis 78 such that first side 73 and second side 74 of second end 76 are each generally shaped as a right-angled trapezoid. In one non-limiting embodiment, the predetermined acute angle between second face 72 of second end 76 and longitudinal axis 78 is between 5-30 degrees.

Each intermediate arm assembly 60 comprises a pair of intermediate arms 110. Each intermediate arm 110 exhibits: a first end 111; a second end 112 opposing first end 111; a first face 113; a second face 114 opposing first face 113; a first side 115 generally orthogonal to first face 113 and second face 114; and a second side 116 opposing first side 115. Each intermediate arm 110 extends from a respective extension portion 100 in a respective direction and exhibits an acute angle with the respective longitudinal axis 78. Particularly, each intermediate arm 110 curves away from longitudinal axis 78, such that first face 113 is generally convexingly curved and second face 114 is generally concavingly curved. Additionally, each intermediate arm 110 curves away from a plane 79 defined by the respective section 70 such that first side 115 is generally convexingly curved and second side 116 is generally concavingly curved. Thus, each intermediate arm 110 exhibits an acute angle with the respective plane 79, the acute angle measured from first side 115 to plane 79. The curve of intermediate arms 110 reduces the chance of intermediate arms 110 breaking responsive to forces applied to first face 113.

First faces 71 of sections 70 of body 20 are attached to each other. In one embodiment, first faces 71 are flush with each other. In another embodiment, a portion of each of first faces 70 is curved such that a space (not shown) is defined between the respective portions of first faces 70. In one embodiment, as illustrated, a first connection member 35 extends through openings 94 of first end 75 of each section 70, first end 36 of the first connection member 35 extending past second face 72 of a first section 70 and second end 37 of the first connection member 35 extending past second face 72 of the second section 70. Similarly, the second connection member 35 extends through openings 94 of second end 76 of each section 70, first end 36 of the second connection member 35 extending past second face 72 of the first section 70 and second end 37 of the second connection member 36 extending past second face 72 of the second section 70.

As described above, each pair of intermediate arms 110 form a respective intermediate arm assembly 60. Thus, each intermediate arm assembly 60 exhibits an acute angle with longitudinal axis 78, the acute angle measured from first face 113 of the constituent intermediate arms 110, as described above. As further described above, each intermediate arm 110 curves away from the respective plane 79. As a result, second ends 112 of the respective constituent intermediate arms 110 of each intermediate arm assembly 60 are separated by a predetermined distance. Although in the above described embodiment the separation is caused by the curvature of intermediate arms 110 away from each other, this is not meant to be limiting in any way. In another embodiment (not shown), intermediate arms 110 do not curve away from each other. In one further embodiment (not shown), first and second sides 115 and 116 of arms 110 are straight and angled away from the respective plane 79. In another further embodiment, intermediate arms 110 are not angled away from the respective plane 79, rather intermediate arms 110 are rotated away from the respective plane 79 to form the separation between second ends 112 of the respective constituent intermediate arms 110 of each intermediate arm assembly 60.

In one embodiment, as illustrated, intermediate arm assemblies 60 are generally symmetrical on both sides of body 20 and are further generally symmetrical on both sections 70, such that intermediate arms 110 are generally symmetrical in relation to planes 79 and in relation to a plane generally orthogonal to planes 79. The general symmetry of intermediate arms 110 provides balanced resistance about body 20 to migration forces, as will be described below, thereby providing improved resistance to migration and superior anchoring capabilities.

In one preferred embodiment, as illustrated, each intermediate arm 110 comprises a plurality of stacked layers 120. Each layer 120 exhibits: a first end 121; a second end 122 opposing first end 121; a first face 123; and a second face 124 opposing first face 123. Each layer 120 extends from the respective extension portion 100 at first end 121 thereof and curve towards second end 122 thereof. Particularly, first face 123 of each layer 120 generally convexingly curves towards second end 122 thereof and second face 124 of each layer 120 generally concavingly curves towards second end 122 thereof. Layers 120 are stacked such that first face 123 of each layer 120 faces second face 124 of an adjacent layer 120.

In one further embodiment, the length of each layer 120, from the respective extension portion 100 to second end 122, is longer than the length of the adjacent layer 120 which is further away from middle portion 77. Additionally, second end 122 of each layer 120, with the exception of the layer 120 furthest away from middle portion 77, comprises a protrusion 125. Protrusion 125 extends generally orthogonally from a vector 126, vector 126 proceeding along the body center of second end 122 of layer 120, protrusion 125 extending towards second end 122 of the subsequent layer 120 which is further away from middle portion 77. When a force pushes against the layer 120 which is closest to middle portion 77, each layer 120 pushes against the subsequent adjacent layer 120, i.e. against the layer 120 immediately further away from middle portion 77 of body 20, and the movement of each layer 120 is arrested by protrusion 125 of the adjacent layer 120.

The above has been described in an embodiment wherein each layer 120 exhibits a protrusion 125 which extends towards second end 122 of the subsequent layer 120 which is further away from middle portion 77, however this is not meant to be limiting in any way. In another embodiment (not shown), each layer 120 exhibits a protrusion 125 which extends towards second end 122 of the subsequent layer 120 which is closer to middle portion 77. In another embodiment (not shown), no protrusions 125 are provided.

Intermediate arms 110 are each illustrated herein as comprising 4 layers 120, however this is not meant to be limiting in any way and any number of layers 120 can be provided without exceeding the scope. Additionally, intermediate arm assemblies 60 are each illustrated and described herein as comprising a pair of intermediate arms 110, however this is not meant to be limiting in any way. In another embodiment (not shown), only a single intermediate arm 110 is provided for each intermediate arm assembly 60. In another embodiment (not shown), more than two intermediate arms 110, separated from each other by respective predetermined distances, are provided.

In one embodiment, intermediate arms 110 extending from a first section 70 and the first section 70 are each formed of a respective portion of material such that intermediate arms 110 are continuous with the first section 70. Particularly, intermediate arms 110 are not connected and/or welded to the first section 70, rather they are a continuation of the first section 70. Similarly, intermediate arms 110 extending from a second section 70 and sections 70 are each formed of a respective portion of material such that intermediate arms 110 are continuous with the second section 70. In another, alternate, embodiment, each intermediate arm 110 is formed of a separate portion of material and is connected to respective sections 70.

Figure 3A:
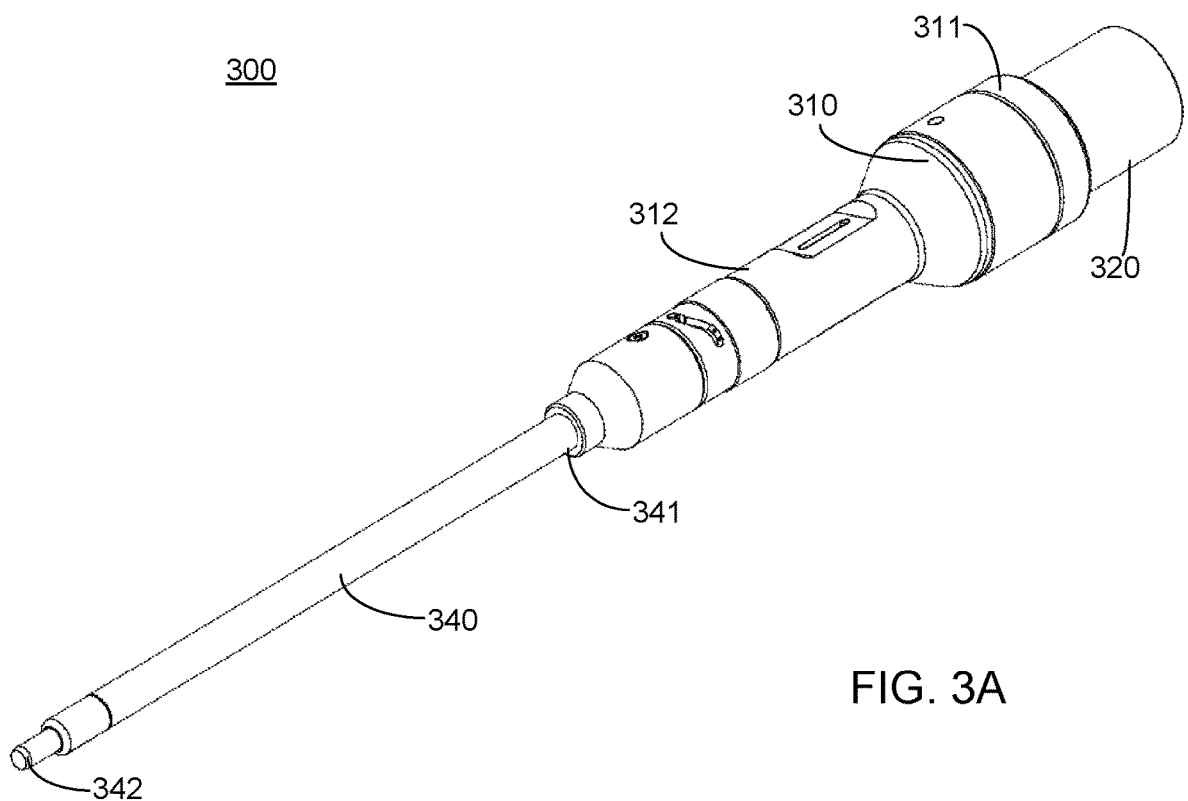
FIGS. 3A-3D illustrate various high level views of a delivery system for the implant of FIGS. 1A-1I, in accordance with certain embodiments.
Figure 3B:
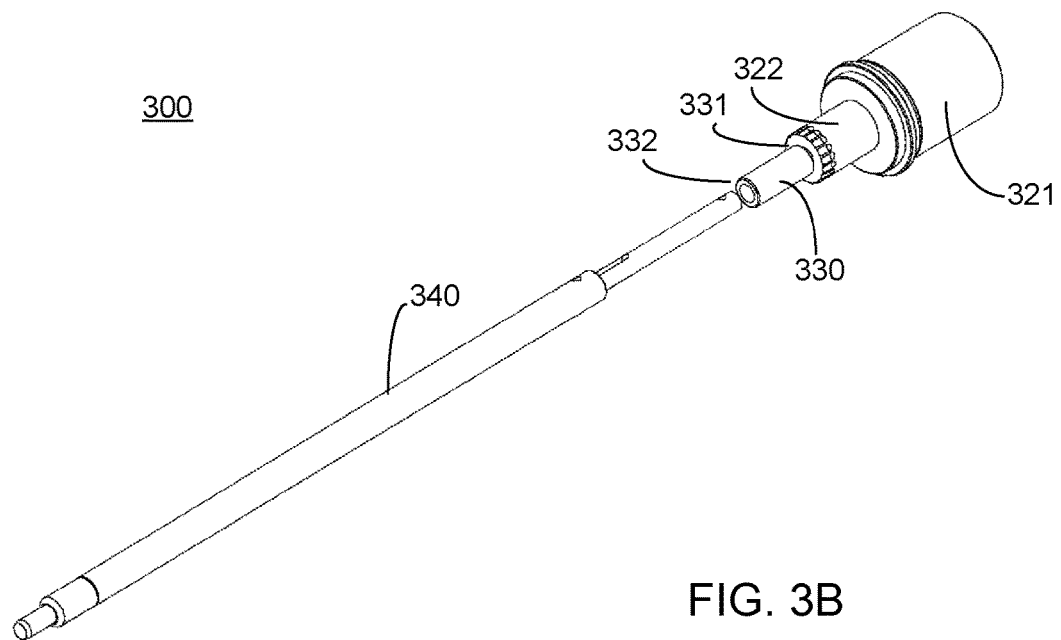
Figure 3C:
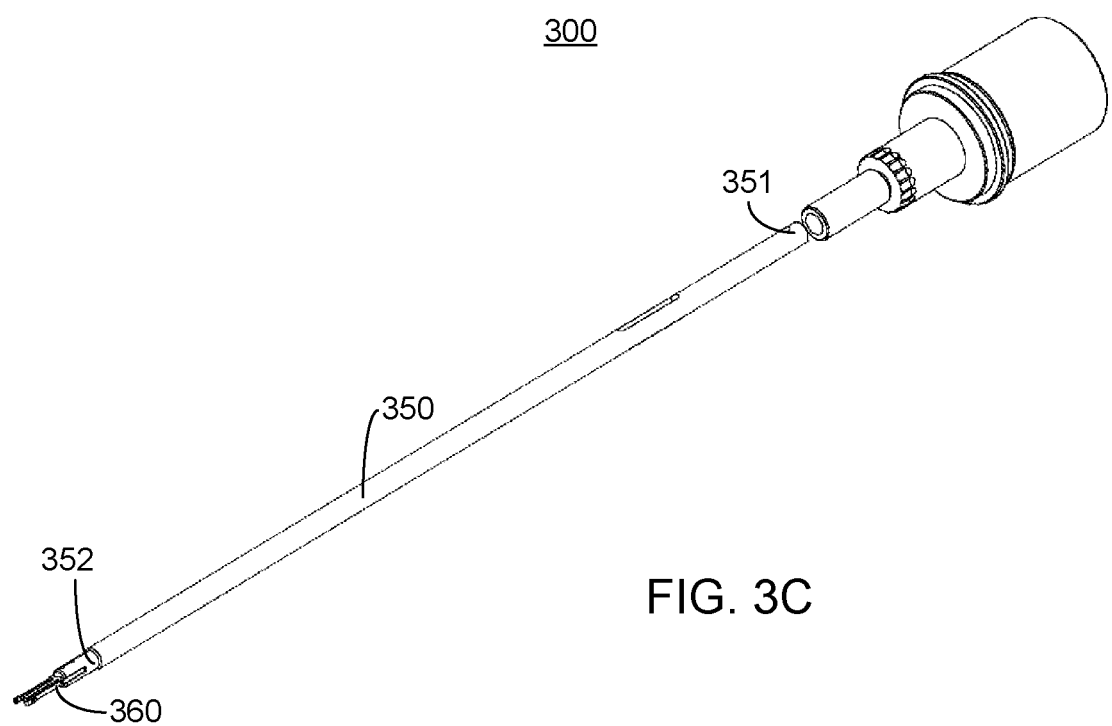
Figure 3D:
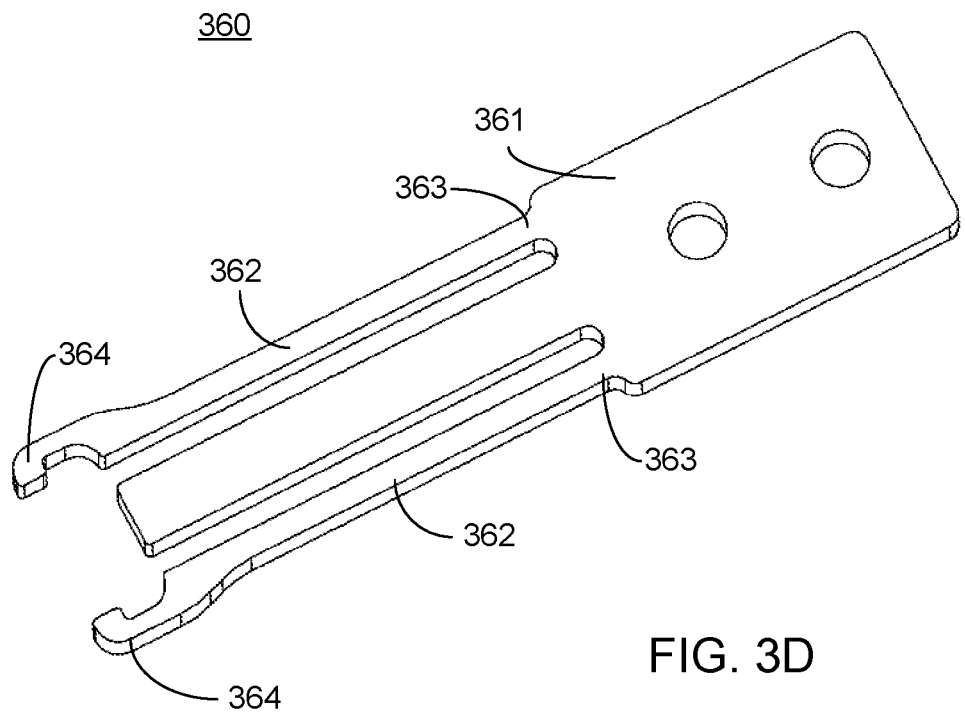
Figure 3E:
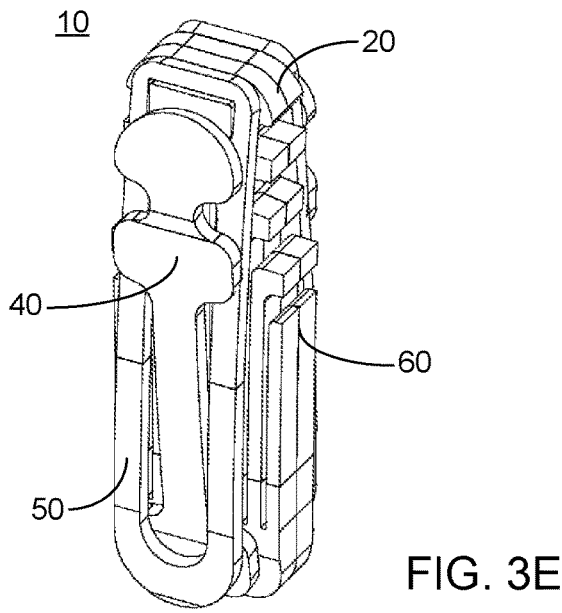
FIG. 3E illustrates a high level perspective view of the implant of FIGS. 1A-1I in a delivery configuration.

In one embodiment, as illustrated in FIG. 3E, each layer 120 is generally rectangular cuboid shaped when in a straight position, however this is not meant to be limiting in any way. In another embodiment (not shown), each layer 120 can exhibit any of plurality of shapes, such as, but not limited to, a generally elliptical shape, a generally triangular shape and a generally circular cross section. In one embodiment, each layer 120 is solid. In another embodiment (not shown), each layer 120 exhibits a plurality of slits along the surface thereof. In one further embodiment, as illustrated in FIG. 1K, each layer 120 exhibits a lattice or mesh configuration, with a generally hollow exterior, similar to a stent.

In one embodiment, as illustrated in FIGS. 1L-1N, each layer 120 comprises a first section 127, a second section 128 and stress release notch 129. First section 127 comprises first end 121 and second section 128 comprises second end 122. Stress release notch 129 is between first section 127 and second section 128. In one particular embodiment, first second 127, second section 128 and stress release notch 129 are formed of a continuous piece of material and are not separate pieces connected together. In one embodiment, as illustrated in FIG. 1L, stress release notch 129 is generally deep u shaped. In another embodiment, as illustrated in FIG. 1M, stress release notch 129 is generally shallow u shaped. In another embodiment, as illustrated in FIG. 1N, stress release notch 129 is generally shallow v shaped. Advantageously, stress release notch 129 provides a release point for stress responsive to pressure applied to layer 120 thereby increasing the amount of pressure which can be applied to layer 120 without cracking.

Each proximal arm 40 extends from second end 76 of a respective section 70 at first end 45 thereof and exhibits a predetermined acute angle with longitudinal axis 30 of body 20, the predetermined acute angle measured between first face 41 and longitudinal axis 30. The extension of proximal arm 40 is towards a plane 130. Plane 130 is orthogonal to longitudinal axis 30 of body 20 and meets first ends 75 of sections 70. In one embodiment, second end 46 of each proximal arm 40 does not extend past plane 130.

In one embodiment, as illustrated, first end 45 of each proximal arm 40 exhibits a respective opening 49 extending from first face 41 to second face 42. In the embodiment described above wherein the second connection member 35 extends through openings 94 of second ends 76 of sections 70, first end 36 of the second connection member 35 extends into opening 49 of a first proximal arm 40 and second end 37 of the second connection member 35 extends into opening 49 of a second proximal arm 40. In one further embodiment, the second connection member 35 is inserted through openings 94 of sections 70 and openings 49 of proximal arms 40 under pressure. Preferably, the second connection member 35 is further connected to openings 49 and 94. In one non-limiting embodiment, the connection is performed by welding or gluing, however any method of providing a firm and permanent assembly can be used.

First face 41 of first end 45 of each proximal arm 40 is juxtaposed with second face 72 of second end 76 of the respective section 70. Preferably, first face 41 of first end 45 is flush with second face 72 of the respective second end 76. As described above, in one embodiment second face 72 of second end 76 exhibits a predetermined acute angle with the respective longitudinal axis 78 such that first side 73 and second side 74 of second end 76 are each generally shaped as a right-angled trapezoid. As a result, when first face 41 of first end 45 is flush with second face 72 of second end 76, the acute angle between the respective proximal arm 40 and longitudinal axis 30 is achieved. Although the above has been described and illustrated in relation to an embodiment where second ends 76 are angled and first ends 45 are straight, this is not meant to be limiting in any way. In another embodiment, first ends 45 are angled instead of, or in addition to, second ends 76, to maintain the acute angle with longitudinal axis 30 without bending proximal arms 40.

In one embodiment, second end 46 of each proximal arm 40 exhibits a first section 140, a second section 141 and a third section 142. Second section 141 is between first section 140 and third section 142. A width of second section 141 is less than a width of each of first section 140 and third section 142. The widths of first, second and third sections 140, 141, 142 are each defined orthogonally to longitudinal axis 48 of the respective proximal arm 40 in the general directions of the extensions of intermediate arms 110. The widths of first, second and third sections 140, 141, 142 further define the distances between first side 43 and second side 44. In one embodiment, the width of second section 141 is generally equal to the width of middle portion 47.

Each distal arm 50 extends from first end 71 of a respective section 70 at first end 53 thereof and exhibits a predetermined acute angle with longitudinal axis 30 of body 20, the predetermined acute angle measured between first face 51 and longitudinal axis 30. The extension of each distal arm 50 is towards a plane 150. Plane 150 is orthogonal to longitudinal axis 30 of body 20 and meets second ends 76 of sections 70. Plane 150 is further generally parallel to plane 130. In one embodiment, second end 54 of each distal arm 50 does not extend past plane 150. Each distal arm 50 extends in a direction generally opposing the direction of a respective proximal arm 40. Particularly, as described above, proximal arms 40 extend towards plane 130 and distal arms 50 extend towards plane 150, body 20 being between plane 130 and plane 150. Thus, the direction of extension of distal arms 50 generally oppose the direction of extension of proximal arms 40. Additionally, in one embodiment, each longitudinal axis 48 of a respective proximal arm 40 is generally parallel to longitudinal axis 56 of a respective distal arm 50 on the opposing side of body 20.

In one embodiment, as illustrated, first end 53 of each distal arm 50 exhibits a respective opening 57 extending from first face 51 to second face 52. In the embodiment described above wherein the first connection member 35 extends through openings 94 of first ends 75 of sections 70, first end 36 of the first connection member 35 extends into opening 57 of a first distal arm 50 and second end 37 of the first connection member 35 extends into opening 57 of a second distal arm 50. In one further embodiment, the first connection member 35 is inserted through openings 94 of sections 70 and openings 57 of distal arms 50 under pressure. Preferably, the first connection member 35 is further connected to openings 57 and 94. In one non-limiting embodiment, the connection is performed by welding or gluing, however any method of providing a firm and permanent assembly can be used.

First face 51 of first end 53 of each distal arm 50 is juxtaposed with second face 72 of first end 75 of the respective section 70. Preferably, first face 51 of first end 53 is flush with second face 72 of the respective first end 76. As described above, in one embodiment second face 72 of first end 75 exhibits a predetermined acute angle with the respective longitudinal axis 78 such that first side 73 and second side 74 of first end 75 are each generally shaped as a right-angled trapezoid. As a result, when first face 51 of first end 53 is flush with second face 72 of first end 75, the acute angle between the respective distal arm 50 and longitudinal axis 30 is achieved. Although the above has been described and illustrated in relation to an embodiment where first ends 75 are angled and first ends 53 are straight, this is not meant to be limiting in any way. In another embodiment, first ends 53 are angled instead of, or in addition to, first ends 75, to maintain the acute angle with longitudinal axis 30 without bending distal arms 50.

In one embodiment, each distal arm 50 further exhibits an opening 58 extending from first face 51 to second face 52. Opening 58 further extends along middle portion 55 between first end 53 and second end 54. In such an embodiment, each proximal arm 40 extends through opening 58 of the respective distal arm 50. In another embodiment (not shown), middle portion 55 of each distal arm 50 is positioned alongside middle portion 47 of proximal arm 40.

As illustrated, in one embodiment, intermediate arm assemblies 60 are rotated about longitudinal axis 30 from the extension directions of proximal arms 40. Specifically, as illustrated, intermediate arms 10 of a first intermediate arm assembly 60 extend in a direction generally orthogonal to longitudinal axis 30 and intermediate arms 10 of the second intermediate arm assembly 60 extend in a direction generally opposing the direction of extension of the first intermediate arm assembly 60. The directions of extension of proximal arms 40 define a plane which is orthogonal to the directions of extension of intermediate arm assemblies 60.

In another embodiment, the thickness of each layer 120 of intermediate arms 110, i.e. the distance between first face 123 and second face 124 thereof, is greater than the thickness of each proximal arm 40 and distal arm. Specifically, the thickness of each proximal arm 40 is defined as the distance between first face 41 and second face 42 and the thickness of each distal arm 50 is defined as the distance between first face 51 and second face 52.

Although the above has been described and illustrated in an embodiment wherein intermediate arms 110 are curved and proximal and distal arms 40, 50 are straight, this is not meant to be limiting in any way. In another embodiment (not shown), one or more of proximal arms 40 and distal arms 50 are curved, and one or more of intermediate arms 110 are straight.

Figure 2:
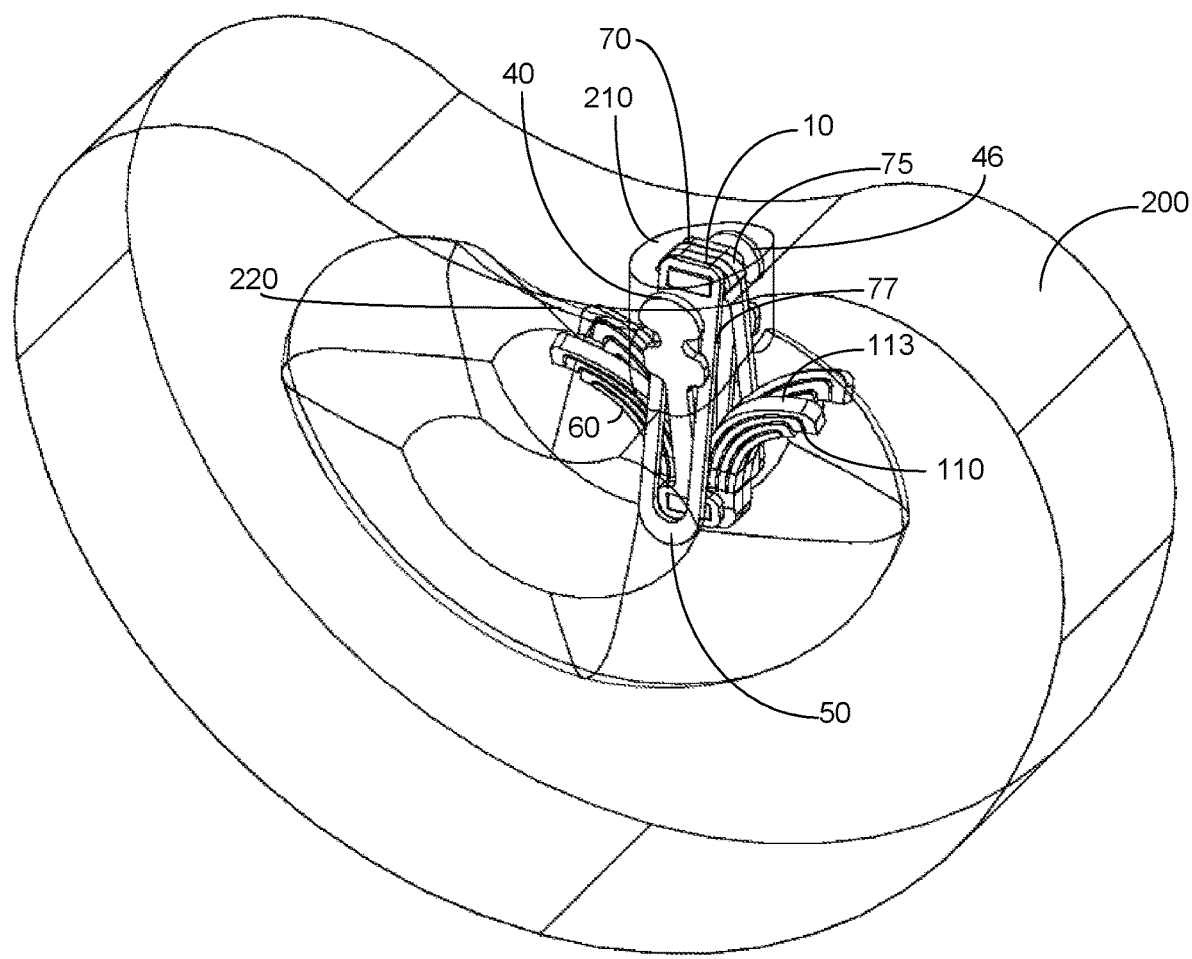
FIG. 2 illustrates a high level perspective view of the implant of FIGS. 1A-1I deployed in a target annulus, in accordance with certain embodiments.

The above has been described in relation to a deployed configuration of implant 10, wherein implant 10 is deployed and performing closure of a biological defect. For example, as illustrated in FIG. 2, implant 10 is deployed within a target annulus 200. Target annulus 200 exhibits a tear 210. Tear 210 is optionally further surgically widened. Implant 10 is positioned such that first ends 75 of sections 70 and second ends 46 of proximal arms 40 are within tear 210. Intermediate arm assemblies 60 are juxtaposed with tear 210 such that first face 113 of the intermediate arms 110 closest to middle portions 77 face an inner wall 220 in the vicinity of tear 210. Intermediate arms 110, proximal arms 40 and distal arms 50 together provide a variety of anchoring points for implant 10 to withstand and oppose forces applied to implant 10 from annulus 200, thereby preventing migration of implant 10 within or out of annulus 200. In one preferred embodiment, proximal arms 40, distal arms 50 and intermediate arm assemblies 60 are each constructed such that when deployed within target annulus 200 they are not completely open. In the embodiment described above wherein a space is provided between middle portions 77 of sections 70, the space further provides a spring-like resistance to forces along longitudinal axis 30.

As described above, in the embodiment where intermediate arms 110 are generally symmetrical about planes 79 and about a plane generally orthogonal thereto, the symmetry provides more balanced resistance about body 20 to migration forces, thereby providing improved resistance to migration and superior anchoring capabilities.

Implant 10 thus blocks nucleus pulposus from exiting target annulus 200 via tear 210. Additionally, implant 10 further acts as a chassis for the growth of scar tissue at tear 210. Second ends 46 of proximal arms 40 are positioned within, or adjacent to, tear 210. Thus, scar tissue can grow on proximal arms 40. Additionally, as described above, first ends 75 of sections 70 are positioned between second ends 46 of proximal arms 40, thereby adding additional material for scar tissue to grow thereon. In the embodiment described above wherein a space is provided between middle portions 77 of sections 70, the space further provides an additional chassis point for scar tissue growth. Furthermore, scar tissue can grow over any of proximal arms 40, distal arms 50, intermediate arm assemblies 60 and sections 70, thus providing a scar tissue growth chassis over an expanded area within the vicinity of tear 210.

FIGS. 3A-3D illustrate various high level perspective views of one non-limiting embodiment of a delivery system 300. Delivery system 300 comprises: a body 310 exhibiting a first end 311 and a second end 312 opposing first end 311; a knob 320 exhibiting a handle 321 and an extension member 322; an advancement member 330 exhibiting a first end 331 and a second end 332 opposing 331; a delivery tube 340 exhibiting a first end 341 and a second end 342; a delivery rod 350 exhibiting a first end 351 and a second end 352 opposing first end 351; and an implant grip 360 comprising a base 361; and a pair of grippers 362. Each gripper 362 exhibits a first end 363 and a second end 364 opposing first end 363. FIG. 3B illustrates a high level perspective view of delivery system 300 without body 310. FIG. 3C illustrates a high level perspective view of delivery system 300 without body 310 and without delivery tube 340. FIG. 3D illustrates a high level perspective view of implant grip 360.

First end 311 of body 310 is juxtaposed with handle 321 of knob 320 and extension member 322 of knob 320 is inserted into first end 311 of body 310. First end 331 of advancement member 330 is coupled to extension member 322 of knob 320 and is inserted into first end 311 of body 310. Delivery rod 350 and implant grip 360 are inserted into delivery tube 340. Second end 332 of advancement member 330 is coupled to first end 351 of delivery rod 350, within body 310, and second end 352 of delivery rod 350 is coupled to base 361 of implant grip 360, within delivery tube 340. First end 341 of delivery tube 340 is juxtaposed with second end 312 of body 310. First end 363 of each gripper 362 extends from base 361. Second ends 364 of grippers 362 face each other and are arranged to grip first ends 75 of sections 70 of implant 10. As described above, first section 90 extends orthogonally to longitudinal axis 78 past first side 73 and past second side 74 of second section 92. Second ends 364 of grippers 362 grip the extended portions of first section 90. Grippers 362 are arranged to be pushed towards each other due to the inner diameter of delivery tube 340 which is smaller than the resting distance between grippers 362.

Delivery tube 340 maintains implant 10 in a delivery configuration. Particularly, in the delivery configuration, as illustrated in FIG. 3E, the angles of proximal arms 40, distal arms 50 and intermediate arm assemblies 60 are significantly reduced, i.e. proximal arms 40, distal arms 50 and intermediate arm assemblies are folded up against body 20.

In operation, tear 210 of annulus 200 is surgically expanded to create a channel. Second end 342 of delivery tube 340 is inserted into surgically expanded tear 210. Handle 321 of knob 320 is rotated by a surgeon, the rotation thereof rotates extension member 322 which in turn advances advancement member 330. Advancement member 330 pushes delivery rod 350 into tear 210. When grippers 362 have exited second end 342 of delivery tube 340, the expand outwards towards their resting positions, thereby releasing implant 10 into tear 210. Additionally, as implant 10 exits second end 342 of delivery 340, implant 10 opens into the deployed configuration, as described above. Delivery system 300 is then retracted from tear 210.

Figure 4:
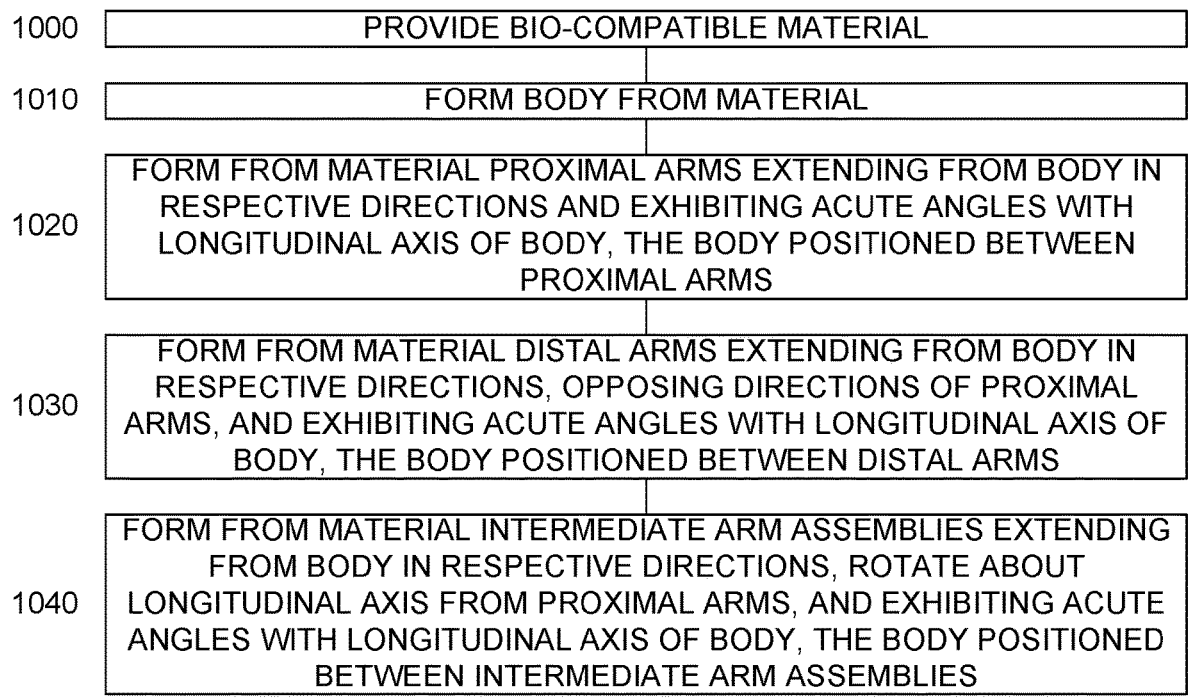
FIG. 4 illustrates a high level flow chart of a method for production of an implant, in accordance with certain embodiments.

FIG. 4 illustrates a high level flow chart of a method for production of an implant. In stage 1000, a bio-compatible material is provided. In stage 1010, a body is formed from the provided bio-compatible material of stage 1000, the formed body exhibiting a longitudinal axis. In stage 1020, a pair of proximal arms are formed from the provided bio-compatible material of stage 1000, the pair of proximal arms extending from the formed body of stage 1010 in a respective direction and exhibiting a respective acute angle with the longitudinal axis of stage 1010, the body positioned between the pair of proximal arms.

In stage 1030, a pair of distal arms are formed from the provided bio-compatible material of stage 1000, the pair of distal arms extending from the formed body of stage 1010, each of the pair of distal arms extending in a direction generally opposing the extension direction of a respective one of the pair of proximal arms and exhibiting a respective acute angle with the longitudinal axis. The body is positioned between the pair of distal arms.

In stage 1040, a pair of intermediate arm assemblies are formed from the provided bio-compatible material of stage 1000, the formed pair of intermediate arm assemblies extending from the formed body of stage 1010, each of the pair of intermediate arm assemblies extending in a respective direction rotated about the longitudinal axis of the body from the respective extension directions of the pair of proximal arms and exhibiting a respective acute angle with the longitudinal axis. The body is positioned between the pair of formed intermediate arm assemblies.

Although the above has been described in relation to an implant comprising a pair of proximal arms, a pair of distal arms and a pair of intermediate arm assemblies, this is not meant to be limiting in any way. Particularly, any number of proximal arms, distal arms and intermediate arm assemblies can be provided without exceeding the scope. Preferably, an even number of proximal arms, an even number of distal arms and an even number of intermediate arm assemblies is provided.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. An implant, the implant comprising:
   a body exhibiting a longitudinal axis;
   a pair of proximal arms extending from said body, each of said pair of proximal arms extending in a respective direction and exhibiting a respective acute angle with said longitudinal axis, said body positioned between said pair of proximal arms;
   a pair of distal arms extending from said body, each of said pair of distal arms extending in a respective direction and exhibiting a respective acute angle with said longitudinal axis, said respective directions of extension of said pair of distal arms generally opposing said respective directions of extension of said pair of proximal arms, said body positioned between said pair of distal arms; and
   a pair of intermediate arm assemblies extending from said body, each of said pair of intermediate arm assemblies extending in a respective direction rotated about said longitudinal axis from said respective extension directions of said pair of proximal arms and exhibiting a respective acute angle with said longitudinal axis, said body positioned between said pair of intermediate arm assemblies,
   wherein each of said pair of intermediate arm assemblies comprises a pair of intermediate arms each exhibiting a first end and a second end opposing said first end, each of said intermediate arms respectively extending from said body at said first end,
   wherein said second ends of respective constituent intermediate arms of each pair of intermediate arm assemblies are separated by a predetermined distance, and
   wherein respective constituent intermediate arms of each of said pair of intermediate arm assemblies curve away from each other.

2. An implant, the implant comprising:
   a body exhibiting a longitudinal axis;
   a pair of proximal arms extending from said body, each of said pair of proximal arms extending in a respective direction and exhibiting a respective acute angle with said longitudinal axis, said body positioned between said pair of proximal arms;
   a pair of distal arms extending from said body, each of said pair of distal arms extending in a respective direction and exhibiting a respective acute angle with said longitudinal axis, said respective directions of extension of said pair of distal arms generally opposing said respective directions of extension of said pair of proximal arms, said body positioned between said pair of distal arms; and
   a pair of intermediate arm assemblies extending from said body, each of said pair of intermediate arm assemblies extending in a respective direction rotated about said longitudinal axis from said respective extension directions of said pair of proximal arms and exhibiting a respective acute angle with said longitudinal axis, said body positioned between said pair of intermediate arm assemblies,
   wherein each of said pair of intermediate arm assemblies exhibits:
      a generally convexingly curved face facing said extension directions of said pair of proximal arms; and
      a generally concavingly curved face facing said extension directions of said pair of distal arms,
   wherein each of said pair of intermediate arm assemblies comprises a plurality of stacked layers, each of said plurality of stacked layers exhibiting a generally concavingly curved face and a generally convexingly curved face opposing said generally concavingly curved face,
   wherein each of said plurality of stacked layers is adjacent to another of said plurality of stacked layers such that said generally concavingly curved face of a first of said adjacent layers faces said generally convexingly curved face of a second of said adjacent layers, and
   wherein said first of said adjacent layers is arranged to push against said second of said adjacent layers responsive to a force being applied to said convexingly curved face of said first of said adjacent layers.

3. The implant of claim 2, wherein each of said plurality of stacked layers comprises a first section, a second section and a stress release notch between said first section and said second section.

4. An implant, the implant comprising:
   a body exhibiting a longitudinal axis;
   a pair of proximal arms extending from said body, each of said pair of proximal arms extending in a respective direction and exhibiting a respective acute angle with said longitudinal axis, said body positioned between said pair of proximal arms;
a pair of distal arms extending from said body, each of said pair of distal arms extending in a respective direction and exhibiting a respective acute angle with said longitudinal axis, said respective directions of extension of said pair of distal arms generally opposing said respective directions of extension of said pair of proximal arms, said body positioned between said pair of distal arms; and
a pair of intermediate arm assemblies extending from said body, each of said pair of intermediate arm assemblies extending in a respective direction rotated about said longitudinal axis from said respective extension directions of said pair of proximal arms and exhibiting a respective acute angle with said longitudinal axis, said body positioned between said pair of intermediate arm assemblies,
wherein each of said pair of proximal arms and each of said pair of distal arms extend linearly from a respective first end to a respective second end, the respective first ends opposing the respective second ends.

5. An implant, the implant comprising:
a body exhibiting a longitudinal axis;
a pair of proximal arms extending from said body, each of said pair of proximal arms extending in a respective direction and exhibiting a respective acute angle with said longitudinal axis, said body positioned between said pair of proximal arms;
a pair of distal arms extending from said body, each of said pair of distal arms extending in a respective direction and exhibiting a respective acute angle with said longitudinal axis, said respective directions of extension of said pair of distal arms generally opposing said respective directions of extension of said pair of proximal arms, said body positioned between said pair of distal arms; and
a pair of intermediate arm assemblies extending from said body, each of said pair of intermediate arm assemblies extending in a respective direction rotated about said longitudinal axis from said respective extension directions of said pair of proximal arms and exhibiting a respective acute angle with said longitudinal axis, said body positioned between said pair of intermediate arm assemblies,
wherein a first of one of said pair of proximal arms and pair of distal arms exhibits an opening, and
wherein a first of the other of said pair of proximal arms and said pair of distal arms is arranged to extend through said opening.

6. An implant, the implant comprising:
a body exhibiting a longitudinal axis;
a pair of proximal arms extending from said body, each of said pair of proximal arms extending in a respective direction and exhibiting a respective acute angle with said longitudinal axis, said body positioned between said pair of proximal arms;
a pair of distal arms extending from said body, each of said pair of distal arms extending in a respective direction and exhibiting a respective acute angle with said longitudinal axis, said respective directions of extension of said pair of distal arms generally opposing said respective directions of extension of said pair of proximal arms, said body positioned between said pair of distal arms; and
a pair of intermediate arm assemblies extending from said body, each of said pair of intermediate arm assemblies extending in a respective direction rotated about said longitudinal axis from said respective extension directions of said pair of proximal arms and exhibiting a respective acute angle with said longitudinal axis, said body positioned between said pair of intermediate arm assemblies,
wherein each of said pair of proximal arms exhibits a first end and a second end opposing said first end, each of said pair of proximal arms respectively extending from said body at said first end,
wherein said second end of one of said pair of proximal arms exhibits a first section, a second section and a third section, said second section being between said first section and said third section, and
wherein a width of said second section is less than a width of each of said first section and said third section, said widths of said first, second and third sections defined orthogonally to a longitudinal axis of said one of said pair of proximal arms.

7. An implant, the implant comprising:
a body exhibiting a longitudinal axis;
a pair of proximal arms extending from said body, each of said pair of proximal arms extending in a respective direction and exhibiting a respective acute angle with said longitudinal axis, said body positioned between said pair of proximal arms;
a pair of distal arms extending from said body, each of said pair of distal arms extending in a respective direction and exhibiting a respective acute angle with said longitudinal axis, said respective directions of extension of said pair of distal arms generally opposing said respective directions of extension of said pair of proximal arms, said body positioned between said pair of distal arms; and
a pair of intermediate arm assemblies extending from said body, each of said pair of intermediate arm assemblies extending in a respective direction rotated about said longitudinal axis from said respective extension directions of said pair of proximal arms and exhibiting a respective acute angle with said longitudinal axis, said body positioned between said pair of intermediate arm assemblies,
wherein each of said pair of proximal arms exhibits a first end and a second end opposing said first end, each of said pair of proximal arms respectively extending from said body at said first end,
wherein each of said pair of distal arms exhibits a first end and a second end opposing said first end, each of said pair of distal arms respectively extending from said body at said first end,
wherein said body exhibits a first end and a second end opposing said first end, each of said pair of proximal arms extending from said second end of said body towards a respective plane, said respective plane orthogonal to said longitudinal axis of said body and meets said first end of said body, and
wherein each of said pair of distal arms extends from said first end of said body towards a respective plane, said respective plane orthogonal to said longitudinal axis of said body and meets said second end of said body.

8. The implant of claim 7, further comprising a connection member, said connection member exhibiting a first end and a second end opposing said first end,
wherein said body exhibits a first face extending from said first end of said body to said second end of said body, and a second face opposing said first face, said second face extending from said first end of said body to said second end of said body, wherein one of said first end and said second end of said body exhibits an opening extending from said first face to said second face, and wherein said first end of one of:
- said constituent arms of said pair of proximal arms; and
- said constituent arms of said pair of distal arms, exhibits a respective opening, said connection member further arranged to extend through said respective opening and through said opening of said body.

9. The implant of claim 7, wherein said body exhibits a first face and a second face opposing said first face, each of said first face and said second face exhibiting a respective acute angle with said longitudinal axis of said body at one of said first end and second end thereof, each of said respective angles of said first face and said second face being equal to said angle between said longitudinal axis of said body and said respective one of said proximal arms and distal arms extending therefrom.

\* \* \* \* \*